(12) United States Patent  (10) Patent No.: US 7,976,568 B2
Cheung et al.  (45) Date of Patent:  Jul. 12, 2011

(54) DEVICE FOR CORRECTING SPINAL DEFORMITIES

(75) Inventors: Kenneth M. Cheung, Hong Kong (CN); Kelvin W. K. Yeung, Hong Kong (CN); Chi Yuen Chung, Hong Kong (CN); William W. Lu, Hong Kong (CN)

(73) Assignees: University of Hong Kong, Hong Kong (HK); City University of Hong Kong, Kowloon (HK)

( * ) Notice: Subject to any disclaimer, the term of this patent is extended or adjusted under 35 U.S.C. 154(b) by 773 days.

(21) Appl. No.: 10/648,158

(22) Filed: Aug. 25, 2003

(65) Prior Publication Data
US 2004/0106921 A1  Jun. 3, 2004

Related U.S. Application Data

(60) Provisional application No. 60/406,019, filed on Aug. 25, 2002.

(51) Int. Cl.
*A61B 17/70* (2006.01)
(52) U.S. Cl. ........................................... 606/279
(58) Field of Classification Search .......... 606/247–279, 606/300–331
See application file for complete search history.

(56) References Cited

U.S. PATENT DOCUMENTS

| | | | | |
|---|---|---|---|---|
| 5,290,289 A | * | 3/1994 | Sanders et al. | 606/279 |
| 5,672,175 A | * | 9/1997 | Martin | 606/61 |
| 6,296,643 B1 | * | 10/2001 | Hopf et al. | 606/263 |
| 6,488,683 B2 | * | 12/2002 | Lieberman | 606/61 |
| 6,592,605 B2 | * | 7/2003 | Lenker et al. | 606/200 |
| 6,706,044 B2 | * | 3/2004 | Kuslich et al. | 606/261 |
| 6,761,719 B2 | * | 7/2004 | Justis et al. | 606/255 |
| 6,783,527 B2 | * | 8/2004 | Drewry et al. | 606/254 |
| 6,802,844 B2 | * | 10/2004 | Ferree | 606/61 |
| 7,008,422 B2 | * | 3/2006 | Foley et al. | 606/61 |
| 7,027,875 B2 | * | 4/2006 | Siess et al. | 607/116 |

(Continued)

FOREIGN PATENT DOCUMENTS
EP  470660 A1 * 2/1992

OTHER PUBLICATIONS

Nitinol Technology, Archived Jun. 4, 2001; pp. 1-3.*

(Continued)

*Primary Examiner* — Thomas C Barrett
*Assistant Examiner* — Christopher Beccia
(74) *Attorney, Agent, or Firm* — Cohen Pontani Lieberman & Pavane LLP

(57) ABSTRACT

The present invention relates generally to a device of and a method for correcting spinal deformities, such as scoliosis and kyphosis. The invention employs the superelasticity or pseudoelasticity, such as found in a nickel-titanium alloy, to provide a continuous, predictable, and controllable correction force and to achieve a gradual and full correction. The correction force can be exerted on the deformed spine either at the time of the spine surgery or after the surgery or both, to afford a full or substantially full correction. The continuous and controllable correction force of the present invention is safer than an instantaneous and large correction force applied only at the time of surgery. Additionally, the continuous and controllable correction force is capable of gradually and fully correcting the spinal deformities without any post-operative manipulation of the correction device or re-operation.

25 Claims, 7 Drawing Sheets

U.S. PATENT DOCUMENTS

2003/0083749 A1* 5/2003 Kuslich et al. ............. 606/61
2003/0220643 A1* 11/2003 Ferree ...................... 606/61

OTHER PUBLICATIONS

Duerig et al, Designing with the Shape Memory Effect, 1989, pp. 581-597, accessed from www.nitinol.com.*

Duerig, Applications of Shape Memory, 1990, pp. 679-692, accessed from www.nitinol.com.*

Stoeckel et al, Superelastic Ni-Ti Wire, Mar. 1991, pp. 45-50, access from www.nitinol.com.*

Stoeckel, Status and Trends in Shape Memory Technology, 1992, pp. 79-84, accessed from www.nitinol.com.*

Melzer et al, Performance Improvement of Surgical Instrumentation through the Use of Nitinol Materials, 1994, pp. 401-409, accessed from www.nitinol.com.*

Duerig et al, Ti-Ni Shape Memory Alloys, 1994, pp. 1035-1048, accessed from www.nitinol.com.*

Duerig et al, The Use of Superelasticity in Medicine, 1996, accessed from www.nitinol.com.*

Russell, Nitinol Melting and Fabrication, 2001, pp. 1-9, accessed from www.nitinol.com.*

Stockel, Nitinol Medical Devices and Implants, 2001, pp. 531-541, accessed from www.nitinol.com.*

Rahman, Patents on Superelastic Shape Memory Alloy, 2008, 65-67.*

Nitinol Data (http://www.shape-memory-alloys.com/data_nitinol.htm#bodytemperature).*

K.E.K. Yeung et al., "The Use of a New Superelastic Alloy in the Progressive Correction of Scoliosis: Phase 1 Heat Treatment Process", Department of Orthopaedic Surgery, The University of Hong Kong, Department of Physics and Material Science, City University of Hong Kong, HKSAR, China; submitted to the $35^{th}$ Annual Meeting of Scoliosis Research Society Cairns, Australia, Oct. 18-21, 2000 (Proceedings p. 208).

* cited by examiner

DEVICE FOR CORRECTING SPINAL DEFORMITIES

CROSS-REFERENCE TO RELATED APPLICATION

This application claims the benefit of U.S. Provisional Application No. 60/406,019 filed Aug. 25, 2002.

FIELD OF THE INVENTION

The present invention generally relates to a device for and a method of correcting spinal deformities. In particular, the present invention relates a device for and a method of gradually correcting spinal deformities.

BACKGROUND OF THE INVENTION

Various correction systems have been used to correct spinal deformities. For example, the Harrington system, introduced in the early 1950s, employs a distraction rod on the concave side of the deformed spine. The use of the Harrington system and spinal fusion in treating idiopathic scoliosis was found useful for both single and double thoracic curves. However, a loss of lumbar lordosis, or the "flatback" effect, can occur when using the Harrington system along with distraction over the lumbar spine. This effect could be countered by segmental wiring (e.g., sublaminar wiring or wiring of the spinous process) over the instrumented site to retain the lumbar lordosis. Nevertheless, the Harrington system can have limited control of sagittal plane correction, limited derotation, and high rate of hook dislodgment in the lumbar spine, encounter distraction rod fracture, and require postoperative external support.

Armstrong and Connock, and Cotrel and Associates introduced the use of a compression rod on the convex side, which uses transverse traction with Harrington rods to correct deformities. Luque and Jacobs introduced the use of strengthened upper hooks to prevent pull out and increase yield strength of the distraction rod. These configurations helped the Jacobs's system achieve correction in hyperextension.

The Luque system employs a spinal implant for scoliosis correction. The use of the spinal implant involves both convex technique and concave technique. The convex technique is usually used to treat patients with thoracic curve, whereas the concave technique is used on patients with lumbar curve or severe deformity. The Luque system uses sublaminar wiring as multiple segmental fixation points with attachment to a rod and the L-shaped Luque rod. The sublaminar wiring provides fixation at various points along the instrumented area and allows the correction forces to distribute along the spine, thereby lowering the possibility of bone fracture and the need for post-operative immobilization.

The C-D spinal instrumentation system, introduced by Cotrel and Dubousset, employs a dual rod system interlinked by a transverse traction device (DTT), and multiple hooks on each rod. The C-D system was intended to improve thoracic lordosis, preserve lumbar lordosis in the sagittal plane, improve correction in the frontal plane, and minimize loss of correction in case of hook migration or fracture at the bone-metal interface.

Similar spinal correction systems include the Texas Scottish Rite Hospital (TSRH) Universal Spinal Instrumentation and Isola spinal implant system. The TSRH system, in addition to obtaining a better correction of thoracic curves in the sagittal and coronal planes and maintaining lumbar lordosis, also provides rigidity of the implant against axial and torsional forces with its Crosslink™ device. The TSRH system has been used to treat severe scoliotic curves. The Isola spinal implant system was developed from Harrington's principles and designs and assembled with variable screw placement system (VSP). The assembly of this implant is intended to minimize internal or external profiling and increase stability and durability. However, complications associated with iliac screw breakage, transverse connector breakage and screw breakage at the end of constructs have occurred when using the Isola system.

The various conventional correction systems however fail to provide complete correction of scoliotic spines. For example, conventional spinal correction systems, from the earlier Harrington, Jacobs and Luque systems to the later developed systems such as TSRH (SOFAMOR DANEK, US), CD Horizons (SOFAMOR DANEK, US) and ISOLA (DePuyAcroMed, Raynbam, Mass., US) and Moss Miami (DePuy AcroMed), use slightly different techniques to correct scoliosis. Such correction systems can reduce spinal deformity by only 60% to 70%, but a full correction is almost impossible. The use of excessive correction forces in attempting a full correction can cause bony fractures or neurological deficit due to spinal cord damage.

Moreover, none of the conventional correction systems takes into account the viscoelastic behavior of the spine. Viscoelastic properties of the spine relate to its time dependent mechanical effect, i.e., the stiffness of spine decreases over the duration for which the force is applied. Such mechanical effect has been observed in spinal surgery, where the force required to hold tissue in tension decreases gradually during the operation. The correction force applied by the correction system will also decrease as the tissues relax. This loss of tension within the correction systems can cause a partial recurrence of deformity subsequent to the correction. Consequently, conventional correction systems can cause a loss of correction for up to 15% as a result of this effect. Furthermore, because scoliosis correction is carried out instantaneously and only at the time of surgery with no time for the tissues to relax, the load on the spine rises rapidly. The increased load on the corrected spine limits the amount of correction force that is safely possible. Thus, viscoelastic behavior of spinal tissues can limit the amount of correction force and in turn the correction rate. If excessive correction forces are used, they can cause bony fractures. In addition, neurological deficit can occur due to rapid over-stretching of the spinal cord.

Gradual and constant correction forces have been adopted to overcome the deficiency caused by viscoelastic relaxation of spinal tissues. Such correction forces can take up the loss of correction occurred due to the viscoelastic behaviors of biological tissues and effect a gradual correction of the deformity after the initial surgery. Conventional systems providing gradual or constant correction forces nevertheless require some form of repeated surgery or post-operative care, resulting in longer hospitalization as well as patient inconvenience and discomfort.

Other methods in which a gradual but constant force is applied to the scoliotic spine include external halo traction, intermittent open lengthening and shape change from shape memory alloys. For example, the shape memory effect (SME) of nickel-titanium (NiTi) alloy has been used to correct scoliosis in a goat model. However, the mechanical strength of SME was insufficient to fully correct spinal deformities.

Pseudoelasticity, another property of nickel-titanium shape memory alloy, can be useful to overcome the above problem and provide a constant recovery force for deformations within the range of 8%. However, such constant correction forces must be kept low to avoid fracture at the anchoring points or interface of the bone and the implant and avoid neurological deficit.

The present invention provides a device and a method that overcomes the above problems. Additionally or alternatively, the present invention is capable of continuously providing a constant force to the spine even after surgery without post-operative manipulation and until the spine is fully or substantially corrected.

SUMMARY OF THE INVENTION

The present invention relates generally to spinal deformity correction. More specifically, the present invention is capable of providing a constant or substantially constant correction force or a similar correction force and maintaining such correction force constant or substantially constant until spinal deformities are corrected. The present invention can correct various spinal deformities including scoliosis, kyphosis, lordosis, and the rotation around the longitudinal axis of the spine. Additionally or alternatively, the present invention can provide horizontal plane correction of spinal deformities.

The present invention provides a device for and a method of correcting spinal deformities. The correction device is capable of providing a constant and controllable correction force, which can be applied to the deformed spine portion. Such a correction force can be maintained at a constant or substantially constant level until the spinal deformities are corrected. For example, the correction device can be formed by using the pseudoelastic or superelastic properties of a material, such as a NiTi alloy, to provide a constant or substantially constant and controllable correction force. The correction device is capable of completely correcting the spinal deformity at the time of operation or gradually correcting the spinal deformity both during and after the operation. Additionally or alternatively, the correction device can apply a constant or substantially constant correction force subsequent to the surgery, allowing a gradual correction of the spinal deformities.

BRIEF DESCRIPTION OF THE DRAWINGS

The detailed description of the present invention will be better understood in conjunction with the accompanying drawings, wherein like reference characters represent like elements, as follows.

DETAILED DESCRIPTION OF THE INVENTION

Figure 1A:
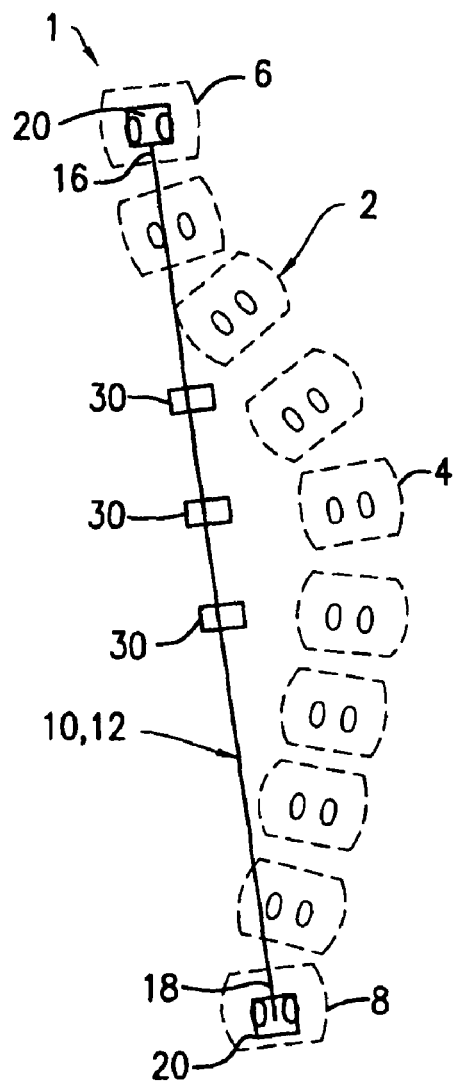
FIGS. 1a and 1b show a first embodiment of the correction device before and after securing elements fix the correction device onto the spine, respectively.

Various correction devices and methods embodying the principles of the present invention will be described below in connection with the accompanying drawings. In the following discussion, same or similar elements are designated with the same numeral references and redundant description will be omitted.

The present invention relates generally to the correction of spinal deformities. According to the present invention, a constant or substantially constant force can be provided for spinal deformity correction. Such a correction force is capable of gradually counteracting the viscoelastic phenomenon of the spine. Accordingly, the present invention is capable of fully or substantially fully correcting spinal deformities. Such correction can be carried out with or without further manipulation of the correction force after the correction force is applied to the deformed spine portion.

For example, a superelastic or pseudoelastic material can be used to provide a constant or substantially constant correction force or a similar force, which can be applied to a deformed spine portion. The constant correction force so provided is capable of gradually and continuously correcting spinal deformities. In an exemplary embodiment, a NiTi alloy can be used to provide a constant or substantially constant and controllable correction force. It will be appreciated that other embodiment of superelastic or pseudoelastic materials are also within the scope of the present invention.

Various methods can be used to form superelastic or pseudoelastic materials that are capable of providing a constant correction force. For example, a superelastic or pseudoelastic material can be formed by mechanically deform or otherwise physically deform a material beyond its elastic limit but within its plastic limit. The material can be allowed to return to the body temperature through heating or gradual warming using any conventional heating mean. Transformation will occur when the material returns to its initial shape to thereby form a superelastic or pseudoelastic material, which can be used for correcting spinal deformities. The transformation can take place instantaneously or over a period of time from several minutes to days. The correction force generated by such a superelastic or pseudoelastic material can maintain a constant or substantially constant level when such a superelastic or pseudoelastic material is subject to deformation within the range of the elastic limit and the plastic limit of the material.

According to the present invention, spinal deformity correction can be carried out in various manners. In an exemplary embodiment, spinal deformities can be completely corrected at the time of operation. In another exemplary embodiment, spinal deformities can be gradually corrected both during and after the operation. For example, a constant or substantially constant correction force can be applied to a deformed spine portion subsequent to the surgery, allowing a gradual correction of the spinal deformities without inducing neurological problems or compromise of the implant-bone interface.

Additionally or alternatively, the spinal deformity correction can be carried out with or without the need for further manipulation. In an exemplary embodiment, a constant or substantially constant and controllable force can be applied to the deformed spine portion with post-operation manipulation. In another exemplary embodiment, a constant or substantially constant and controllable force can be applied to the deformed spine portion post-operatively without the need for further manipulation. It will be appreciated that other embodiments for correcting spinal deformities are also within the scope of the present invention.

Various spinal deformities can be corrected in accordance with the present invention. For example, correction can be directed to the rotation around the longitudinal axis of the spine (apical vertebral rotation or rib hump), which is a typical accompaniment of scoliosis. In an exemplary embodiment, correction can be gradually and fully conducted to correct scoliosis. In another exemplary embodiment, a horizontal plane correction can be achieved.

According to one aspect of the present invention, a correction device can be provided for correcting spinal deformities. The correction device can be formed in various manners. In an embodiment, the correction device can comprise one or more elastic members that is capable of providing a constant or substantially constant correction force. For example, a superelastic or pseudoelastic material can be used to provide a constant or substantially constant correction force. In an exemplary embodiment, the correction device can comprise one or more correction member formed of a superelastic or pseudoelastic or a similar material to afford such a correction force. The superelastic or pseudoelastic material can acquire the required superelasticity or pseudoelasticity, such as by thermal or thermal mechanical treatment. For example, the superelastic or pseudoelastic material can have a transition temperature within the range of body temperature. In an exemplary embodiment, a NiTi alloy can be used. Various manners of constructing the correction device will be described in great detail below.

In one embodiment, the correction device can comprise one or more support members in various forms. For example, the support member can comprise one or more supporting rods of various shapes depending on the sagittal profile of the spine. In one exemplary embodiment, the supporting rod can be contoured to assume the normal degrees of spine kyphosis and lordosis. In another exemplary embodiment, the supporting rod can have such a length to span across the deformed spine portion. In a further exemplary embodiment, the supporting rod can have various cross-sections. For example, the supporting rod can have circular, oval, square, hexagonal, or other shapes or a combination thereof. It will be appreciated that other forms of the supporting rod and the support member are also within the scope of the present invention.

The support member can be placed at various positions in relation to the spine. In an exemplary embodiment, the support member can be provided to extend along at least a portion of the spine. For example, the support member can have such a length to span across the deformed spine portion and bridge the intact vertebrae. Additionally or alternatively, the support member can be placed in the posterior or anterior aspect of the spine in its parent phase (or austenite phase). In an exemplary embodiment, the support member can be provided to extend along the posterior side of the spine. In another exemplary embodiment, the support member can be provided to extend along the anterior side of the spine. It will be appreciated that other embodiments of positioning the support member are also within the scope of the present invention.

The support member can be mounted onto the spine in various manners. For example, the support member can be secured onto the spine by various securing elements, such as one or more bone fasteners. Examples of bone fasteners include, but not limited to, hooks, screws, wires, clamps, and the like. In an exemplary embodiment, the supporting rod can have its free ends mounted onto the spine using various bone fasteners. It will be appreciated that other embodiments of mounting the support member are also within the scope of the present invention.

The support member can be made of various materials. In one exemplary embodiment, the support member can comprise a superelastic or pseudoelastic material capable of providing a constant or substantially constant correction force. After such support member is subjected to deformation force, the deformed support member is capable of providing a constant or substantially constant force, which enables the deformed support member to return to its initial formation upon the release of the deformation force. The constant or substantially constant force so generated can be used to fully or substantially fully correct various spinal deformities. In an exemplary embodiment, the support member can comprise a NiTi alloy. It will be appreciated that other superelastic or pseudoelastic materials are also within the scope of the present invention.

If desired, the magnitude of the correction force can be adjusted or varied in various manners. For example, the correction force can be varied by altering the size and shape of the support member. In one exemplary embodiment, the correction force can be adjusted by using support members of different diameters. In another exemplary embodiment, the correction force can be adjusted by using support members of different cross-sections. Additionally or alternatively, a separate device can be used to adjust the correction force. For example, a braking element can be applied to the support member to dampen the correction force. It will be appreciated that other embodiments of adjusting the magnitude of the correction force are also within the scope of the present invention.

In another embodiment, the correction device can comprise one or more anchor members in various forms. The anchor member is capable of joining a portion of the support member with the spine. For example, upon the completion of spinal correction surgery, the anchor member can mount the support member onto the deformed spine portion to lock the support member in place. Exemplary anchor members can include, but not limited to, hooks, screws, wires, clamps, and the like. In an exemplary embodiment, the anchor member can be partially formed of a superelastic or pseudoelastic material, such as NiTi, or other materials with similar properties.

In one exemplary embodiment, at least one anchor member can be in the form of a transverse traction member. The transverse traction member can be connected between the support member and a vertebra of the spine directly or via another anchor member. The transverse traction member can be formed to provide an independent correction force of a constant or substantially constant value. For example, the transverse traction element can comprise a superelastic or pseudoelastic material or other similar materials. In one exemplary embodiment, the independent correction force generated by the transverse traction member is capable of correcting the spinal deformities without using a superelastic support member. In another exemplary embodiment, the independent correction force generated by the transverse traction member can be used to reinforce, reduce, terminate, or otherwise adjust the correction force generated by the support member. Exemplary transverse traction members can include, but are not limited to, superelastic spring members, adjustable cylinders, internal motors, gear boxes, and the like. It will be appreciated that other embodiments of the transverse traction member and the anchor member are also within the scope of the present invention.

The anchor members can be locked onto the support member and the deformed spine portion in various manners. For example, the locking process can be carried out by tightening the anchor members. In an exemplary embodiment, the locking process can be carried out by using a surgical tool, such as a screw driver, via incision. In another exemplary embodiment, the locking process can be induced remotely without the need for open surgery. For example, the locking process can be carried out by triggering shape change in a NiTi anchor member, such as through heating. In an exemplary embodiment, a heating device, such as an electromagnetic device, can be used to provide the heat. In one exemplary embodiment, the heating device can be applied to the skin in a close proximity to the NiTi anchor member. It will be appreciated that other embodiments of the locking process are also within the scope of the present invention.

According to the present invention, at least one of the support member and the anchor member can be formed as a correction member. The correction member is capable of providing a constant or substantially constant correction force for correcting spinal deformities. The correction device so formed is thus capable of gradually and fully correcting spinal deformities without further manipulation of the correction member after the spinal correction surgery.

If desired, the support member can be restricted from undesired movement or rotation. The restriction can be carried out in various manners. For example, one or more restraining elements can be provided to prevent the support member from undesired movement or rotation. In one exemplary embodiment, the restraining element can comprise one or more locking elements, such as lockable clamps, which are capable of preventing the support member from further movement. Additionally or alternatively, the restraining element can comprise a stopper element to prevent the support member from rotating beyond a pre-defined position. The restraining element can be operated in various manners. In an exemplary embodiment, the restraining element can be operated by a direct access tool, such as a screw driver. In another exemplary embodiment, the restraining element can be operated by a remote access tool, such as an electromagnetic heating device. It will be appreciated that other embodiments of the restraining element are also within the scope of the present invention.

If desired, the correction device can be provided with additional components to reinforce, reduce, terminate, or otherwise adjust the correction force. For example, the correction device can further comprise one or more of the following components: (a) means for alternating the diameter of the support member to control recovery force; (b) one or more internal motor, gear boxes, and the like; and (c) springs or coils or wires made from a superelastic material or other materials with similar properties.

According to another aspect of the present invention, a method is provided for correcting spinal deformities. In one embodiment, a correction force having a predetermined amount can be provided to a deformed spine portion. If desired, the magnitude to the correction force can be adjusted. The correction force can be maintained at a constant or substantially constant level until the spinal deformities are fully corrected. The correction force can be activated either during or after the spine surgery. In an exemplary embodiment, the correction force can be generated by a correction member formed of a superelastic or pseudoelastic material or the like. It will be appreciated that other embodiments of generating the correction force are also within the scope of the present invention.

Various embodiments of the correction device and the correction method will be described in great detail below.

Figure 1B:
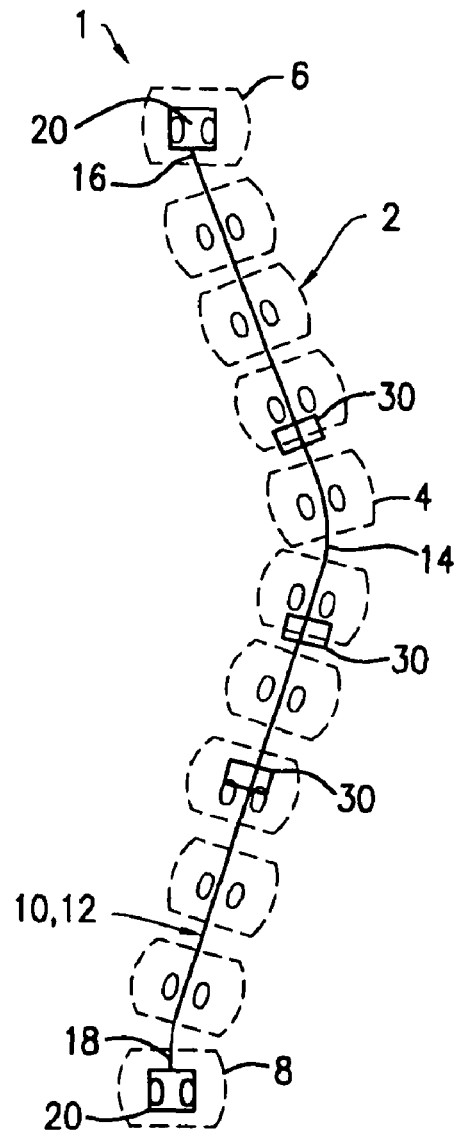

FIGS. 1a and 1b show a first embodiment of the correction device 1 for correcting various spinal deformities, such as scoliosis. The correction device 1 can be in various forms and be mounted onto at least a portion of the spine 2. For example, the correction device 1 can be either applied to the vertebral body anteriorly or applied to elements of the neural arch posteriorly. In one embodiment, the correction device 1 can comprise a support member 10 of various forms. In an exemplary embodiment, the support member 10 can comprise a supporting rod 12 of various shapes. For example, the supporting rod 12 can have a general curved shape, such as a "C" or "S" shape, or other shapes depending on the sagittal profile of the spine. In another exemplary embodiment, the support member 10 can be contoured to conform to the natural spine curvature(s). For example, the support member 10 can be contoured to assume the normal degree of spine kyphosis and/or lordosis. In an exemplary embodiment, such as shown in FIG. 1b, the support member 10 can comprise a curved portion 14, which can be formed such as by bending the support member 10 to conform to a deformed spine portion 4 to be corrected.

The support member 10 can be placed in various positions in relation to the spine 2. In an exemplary embodiment, the support member 10 can be positioned on the posterior side of the vertebrae. In another exemplary embodiment, the curved support member 10 can be positioned on the posterior side of the vertebrae and longitudinally aligned with the vertebrae so that the hump of the curved support member 10 can be positioned at the posterior side of the body.

The support member 10 can be secured to the spine 2 as a support for the correction device 1. For example, the support member 10 can be fixed onto one or more vertebrae by one or more securing elements 20. Exemplary securing elements 20 can include, but are not limited to, hooks, screws, wires, clamps, and the like. In an exemplary embodiment, the support member 10 can be an elongated member, which is capable of spanning the deformed spine portion 4 or otherwise bridging between a proximal end 6 and a distal end 8 of the spine 2. The end portions 16 and 18 of the support member 10 can be fixed to an upper vertebra 6 and a lower vertebra 8 to thereby mount the correction device 1 onto the spine 2. In another exemplary embodiment, the support member 10 can be fixed to the vertebrae at multiple locations.

The support member 10 can be formed of various materials. For example, the support member 10 can be formed of a material that is capable of providing sufficient strength for the correction device 1. In one exemplary embodiment, the support member can comprise an elastic material capable of providing a constant or substantially constant correction force. For example, the support member 10 can be formed of a superelastic or pseudoelastic material, or other materials with similar properties.

In another embodiment, the correction device 1 can comprise one or more anchor members 30 to join the support member 10 with the deformed spine portion 4 to apply a correction force thereto. The anchor members 30 can be in various forms. For example, various bone anchors can be used to join the support member 10 with the deformed spine portion 4. Exemplary anchor members 30 can include, but are not limited to, wires, threads, hooks, screws, clamps and the like. In an exemplary embodiment, one or more anchor members 30 used can be the same as the securing elements 20 discussed above. In another exemplary embodiment, one or more anchor members 30 can be in the form of a transverse traction member 32 (see FIG. 2). Such transverse traction member 32 is capable of providing a constant or substantially constant force for correcting various spinal deformities as will be discussed in detail below.

The anchor members 30 can be used in various manners. In an exemplary embodiment, the anchor members 30 can join the support member 10 with the deformed spine portion 4 at the time of operation. In another exemplary embodiment, one or more anchor members 30 can be linked to at least one of the support member 10 and the deformed spine portion 4 but left unlocked at the time of operation. The unlocked anchor members 30 can later join the support member 10 to the deformed spine portion 4 by various means after the operation.

The correction device 1 is capable of fully or substantially fully correcting spinal deformities. In an exemplary embodiment, the support member 10 can be formed of a superelastic or pseudoelastic material, or other materials with similar properties. One portion 14 of the superelastic support member 10 can be subjected to a deformation force and bent to conform to the deformed spine portion 4. The anchor member 30 can be applied to join the bent portion 14 of the support member 10 and the deformed spine portion 4, such as shown in FIG. 1b. The correction of spine deformities can be achieved by straightening the bent portion 14 in a coronal or sagittal plane. In one exemplary embodiment, the support member 10 is capable of returning to its initial shape and providing a constant or substantially constant correction force in the return process. Additionally or alternatively, a transverse traction member 32 can be provided, which is capable of providing a constant or substantially constant transverse traction force for correcting spine deformities as will be discussed below.

Figure 2:
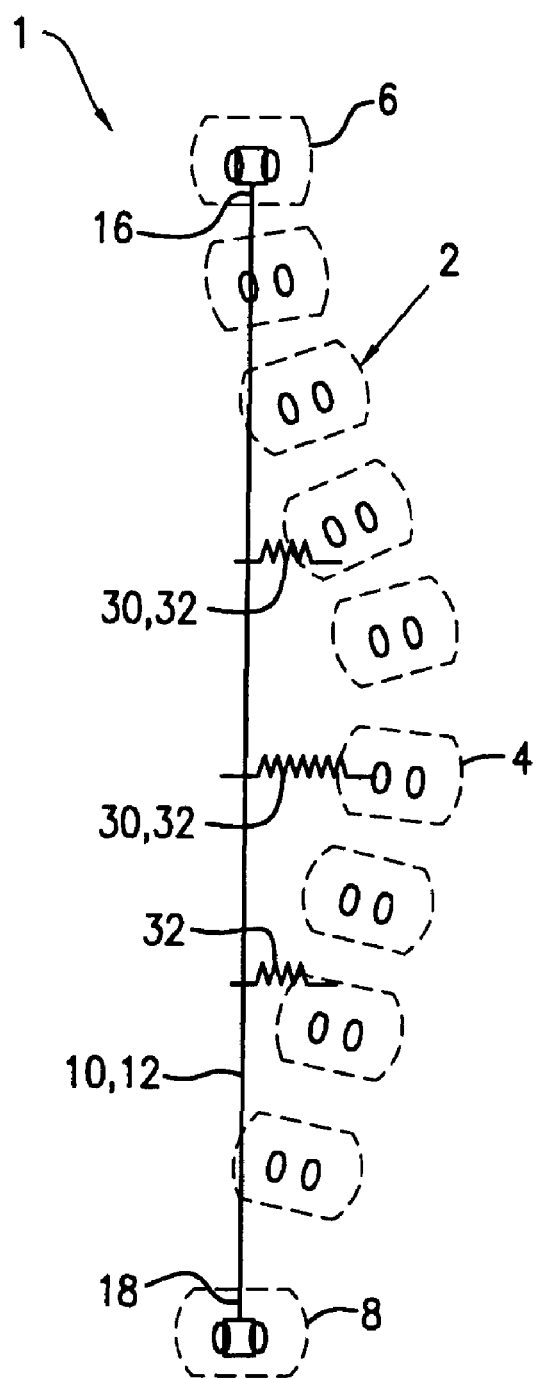
FIG. 2 shows a second embodiment of the correction device, in which a transverse traction member is provided to a single rod system.

FIG. 2 shows a second embodiment of the correction device 1, which is of a single support member type. Similar to the above, the support member 10 can be in a "C" or "S" shape, depending on the sagittal profile of the spine. In an exemplary embodiment, the support member 10 can be longitudinally aligned on the posterior side of the vertebrae. In another exemplary embodiment, the support member 10 can be disposed on the deformed spine 2 extending between a proximal vertebra 6 and a distal vertebra 8. The support member 10 can be mounted onto the spine 2 to provide a support for the correction device 1. In an exemplary embodiment, such as shown in FIG. 2, the two ends 16 and 18 of the support member 10 can be fixed to the proximal vertebra 6 and the distal vertebra 8. In another exemplary embodiment, the support member 10 can be secured to multiple sections of the deformed spine 2.

One or more anchor members 30 can be used to join the support member 10 with the deformed spine portion 4. Similar to the above, the anchor members 30 can be activated to lock the support member 10 and the deformed portion 4 during or after the spine surgery, or both. Additionally or alternatively, the activation can be carried out either by a mechanical device, such as a screw driver or by a remote means, such as an electromagnetic heating.

In an embodiment, such as shown in FIG. 2, one or more anchor members 30 can be in the form of transverse traction members 32. In an exemplary embodiment, one or more transverse traction members 32 can be connected between the support member 11 and one or more vertebrae of the spine 2 via another anchor member 30. The traction members 32 can be in various forms and capable of providing a constant or substantially constant transverse traction force. In an exemplary embodiment, the traction member 32 is capable of reinforcing or reducing the correction force provided by the support member 10. In another exemplary embodiment, the transverse traction member 32 is capable of independently correcting spinal deformities. Exemplary transverse traction members 32 can include, but are not limited to, superelastic spring members, adjustable cylinders, internal motors, gear boxes, and the like.

Figure 3:
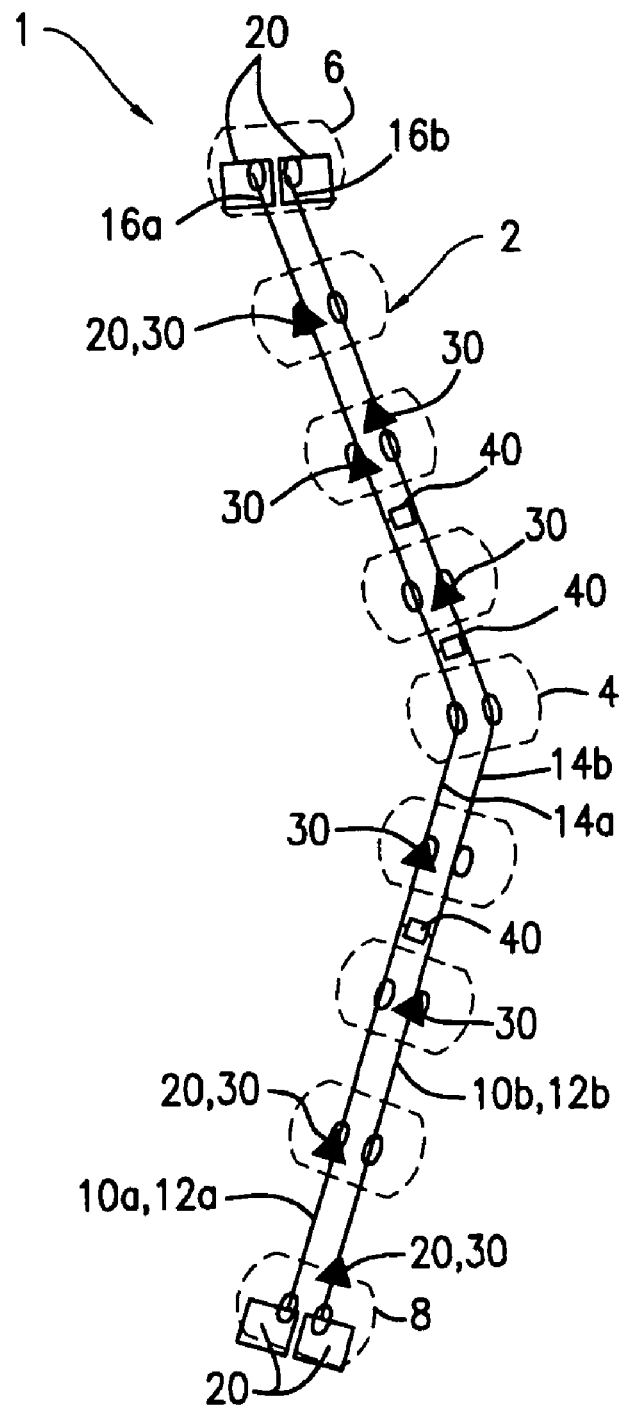
FIG. 3 shows a third embodiment of the correction device, in which a cross-linking element is provided to a dual rod system.

FIG. 3 shows a third embodiment of the correction device 1, which is of a dual support member type. The correction device 1 can comprise first and second support members 10a and 10b, such as in the form of "C" or "S" shaped supporting rods 12a and 12b. The support members 10a and 10b can be disposed in various positions in relation to the deformed spine 2. In one exemplary embodiment, at least one of the support members 10a and 10b can be longitudinally aligned on the posterior side of the spine 2. In another exemplary embodiment, the first and second support members 10a and 10b can fit into the concave and convex sides of the deformed spine portion 4, respectively. If desired, one or more cross-linking elements 40 can be provided to connect between the support members 10a and 10b, such as shown in FIG. 3.

The support members 10a and 10b can be secured to the deformed spine 2 in various manners. In one exemplary embodiment, the support members 10a and 10b can extend from a proximal vertebra 6 to a distal vertebra 8 of the spine 2 and be secured thereonto. For example, the ends 16a and 18a, or 16b and 18b, of the support member 10a or 10b can be fixed to the proximal and distal vertebrae 6 and 8 by various securing elements 20, such as hooks, screws, wires, clamps, and the like. In one exemplary embodiment (not shown), the upper ends 16a and 16b of the support members 10a and 10b can be secured onto different proximal vertebrae. In another exemplary embodiment, each support member 10a or 10b can be secured to multiple sections of the deformed spine 2.

In one exemplary embodiment, at least one of the support members 10a and 10b can be formed of a superelastic or pseudoelastic, or materials with similar properties. In an exemplary embodiment, both support members 10a and 10b can be made of a superelastic material. The superelastic support members 10a and 10b can be bent to form a bent portion 14a and 14b to fit into the deformed spine portion 4, such as shown in FIG. 3. The correction of spine deformities can be achieved by straightening the bent portions 14a and 14b in a coronal or sagittal plane. In an exemplary embodiment, the hump of the bent portions 14a and 14b can be positioned at the posterior side of the body. The bent portions 14a and 14b can be joined to the deformed spine potion 4 in various manners to apply the correction force thereto. In an embodiment, a plurality of anchor members 30 can be used to implant into one or more sections of the deformed spine portion 4 to join the same with the support members 10a and 10b. The anchor members 30 can be locked either at the time of operation or after the operation.

Figure 4:
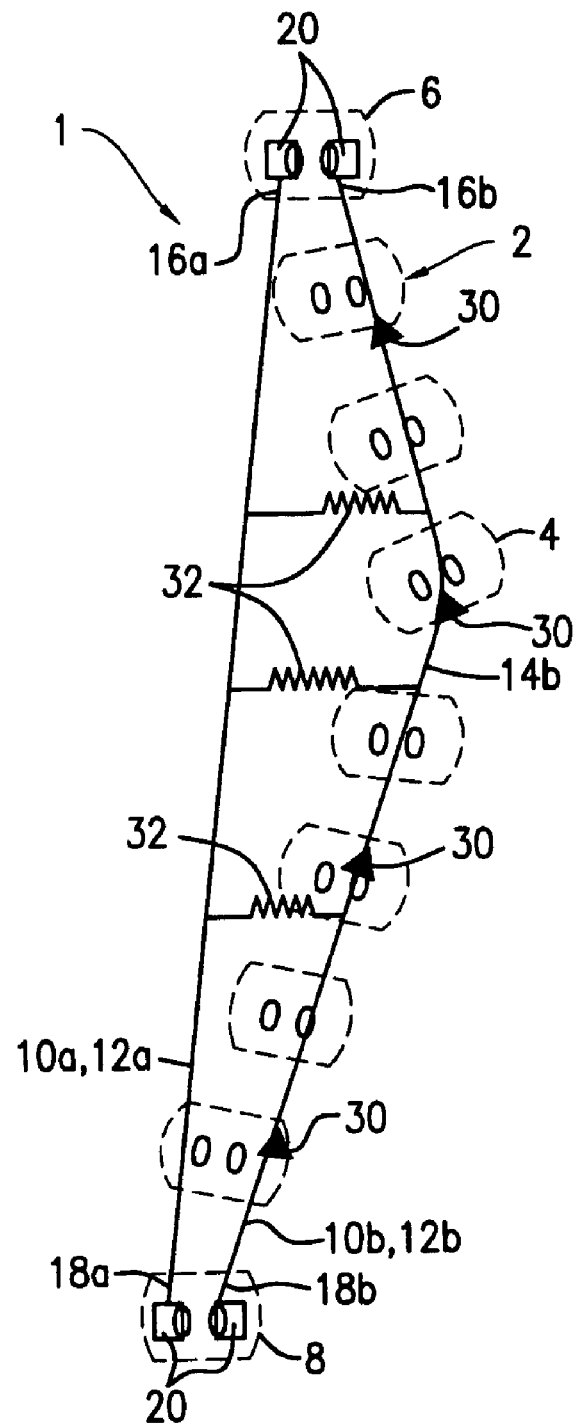
FIG. 4 shows a fourth embodiment of the correction device, in which a transverse traction element or a cross-linking element is provided to a dual rod system.

FIG. 4 shows a fourth embodiment of the correction device 1, which is of a dual support member type. The correction device 1 can comprise first and second support members 10a and 10b, such as "C" or "S" shaped supporting rods 12a and 12b. The support members 10a and 10b can be similarly disposed in various positions in relation to the deformed spine 2. In one exemplary embodiment, one or both of the first and second support members 10a and 10b can be longitudinally aligned on the posterior side of the vertebrae. The support members 10a and 10b can be secured onto the spine 2 through various securing elements, such as hooks, screws, wires, clamps, and the like. In an exemplary embodiment, the upper ends 16a and 16b of the support members 10a and 10b can be fixed to each other and an upper vertebra 6 through wires, hooks, screws, clamps, and the like. In another exemplary embodiment, the first and second support members 10a and 10b can be secured to different upper and/or lower vertebrae 6 and 8.

In one exemplary embodiment, the second support member 10b can be formed of a superelastic material or other materials of comparable properties. The superelastic support member 10b can be deposited on the deformed spine portion 4, such as shown in FIG. 4. In an exemplary embodiment, the second support member 10b can be bent to form a curved portion 14b conforming to the deformed spine portion 4 and join the same through various anchor members 30. For example, the anchor members 30 can be implanted to one or more vertebra to fix the second support member 10b to the deformed spine portion 4. The anchor members 30 can be operated in various manners. In an exemplary embodiment, the anchor members 30 can be left unlocked at the time of the spine surgery and activated to switch to a locked position after the surgery.

In another exemplary embodiment, one or more transverse traction members 32 can be provided to generate an independent constant or substantially constant correction force. In an exemplary embodiment, such as shown in FIG. 4, the transverse traction members 32 can be provided to join between the first and second support members 10a and 10b. In one exemplary embodiment, the transverse traction members 32 are capable of adjusting the magnitude of the correction force generated by the second support member 10b. For example, each transverse traction member 32 can provide an independent correction force to reinforce or reduce the value of the constant correction force so that the correction device 1 is capable of providing a constant correction force of a different value than that generated by the second support member 10b. Exemplary transverse traction members 32 can include, but are not limited to, superelastic spring members, adjustable cylinders, internal motors, gear boxes, and the like.

Figure 5A:
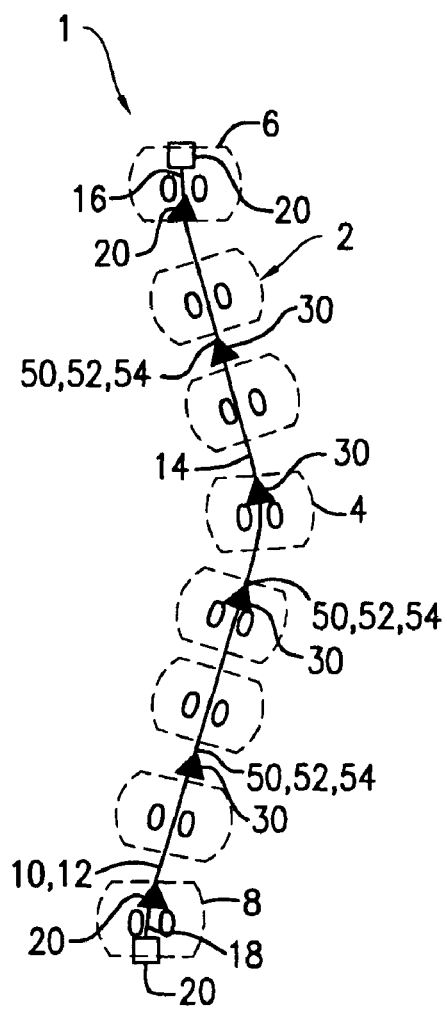
FIGS. 5a and 5b show a fifth embodiment of the correction device, in which a braking element is provided in a single rod system and a dual rod system, respectively.
Figure 5B:
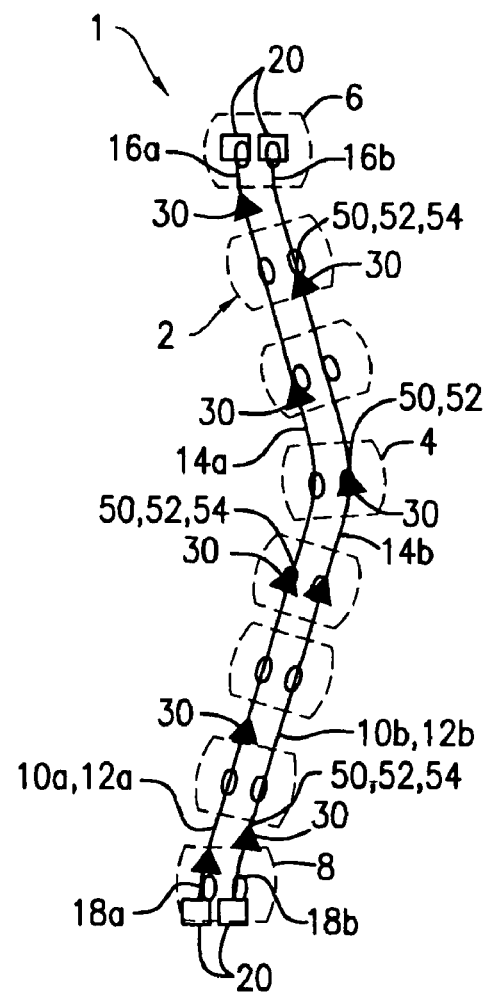

In an exemplary embodiment, such as shown in FIG. 5a or FIG. 5b, one or more braking elements 50 can be provided and formed in various manners to adjust the constant correction force. For example, the braking elements 50 can be attached to any portion of the support member 10 or the anchor members 30 to reduce or terminate the correction force applied to correct scoliosis. Exemplary braking elements 50 can include, but are not limited to, wires, threads, hooks, screws, clamps and the like. In an exemplary embodiment, one or more braking elements 50 can be in the form a clamp 52, such as a "C" shaped clamp. In another exemplary embodiment, the clamp 52 can be at least partially formed of a superelastic or pseudoelastic material or other materials with the same properties. In a further exemplary embodiment, the braking elements 50 can be the same as the anchor member 30.

Additionally or alternatively, one or more braking elements 50 can be formed to provide an adjustable braking force. In an exemplary embodiment, the clamp 52 can be coated with a material, such as polyethylene, on the internal surface thereof to reduce or dissipate the correction force or energy generated by the support member 10. The correction force can be controlled by varying the coating material or the gripping force of the clamp 52. In another exemplary embodiment, one or more braking elements 50 can be in the form of an adjustable screw or washer element 54. Depending on how tight the adjustable screw or washer element 54 is adjusted, the braking element 50 is capable of providing a variable braking force to the support member 10, thereby controlling the correction force. It will be appreciated that other embodiments of the braking elements 50 are also within the scope of the present invention.

Figure 6A:
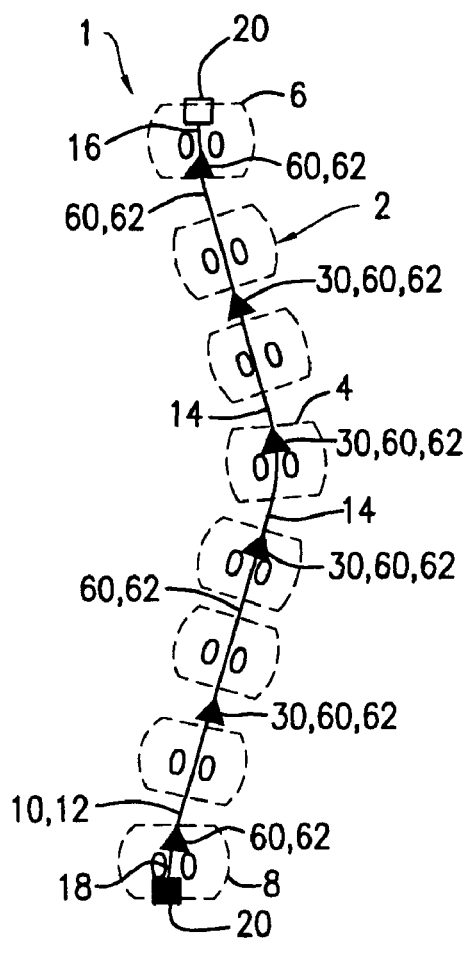
FIGS. 6a and 6b show a sixth embodiment of the correction device, in which a locking element is provided in a single rod system and a dual rod system, respectively.
Figure 6B:
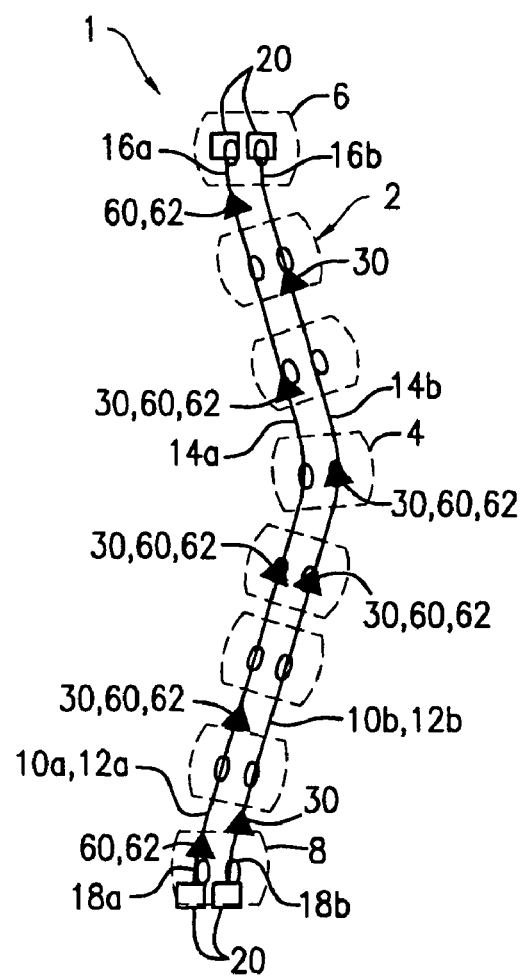

If desired, various accessory elements can be used in the correction device 1. For example, one or more restraining elements 60 can be provided to limit the support member 10 from undesired movement or rotation. The restraining elements 60 can be in various forms. In an exemplary embodiment, such as shown in FIG. 6a or 6b, one or more locking elements 62 can be used to limit the movement of the support members 10, 10a, and 10b. Exemplary locking elements 62 can include, but are not limited to, clamps, lockable clamps or similar devices. In an exemplary embodiment, the locking elements 62 can be in the form of "C" shaped clamps, which is adapted to be placed on the support members 10, 10a, and 10b. The locking elements 62 can be made of various materials, such as an NiTi alloy.

The locking elements 62 can be used in various manners. In an exemplary embodiment, one or more locking elements 62 can be set in a closed position at the time of surgery to retain the support members 10, 10a, and 10b in an appropriate position while other locking elements 62 can be set at an open position. When the spine correction comes to finish or satisfactory, the closed locking elements 62 can be opened and the open locking element 62 can be closed. In another exemplary embodiment, the locking elements 62 can be set in an open position at the time of surgery to retain the support members 10, 10a, and 10b in an appropriate position. When the correction comes to a full or substantially full completion, the locking elements 62 can then be tightened.

The locking and unlocking processes can be activated by various mechanisms, such as by a shape memory effect found in a NiTi alloy or by the use of a mechanical device, such as screws and nuts. Additionally or alternatively, the locking and unlocking processes can be controlled in various manners, such as manually or remotely.

Figure 7A:
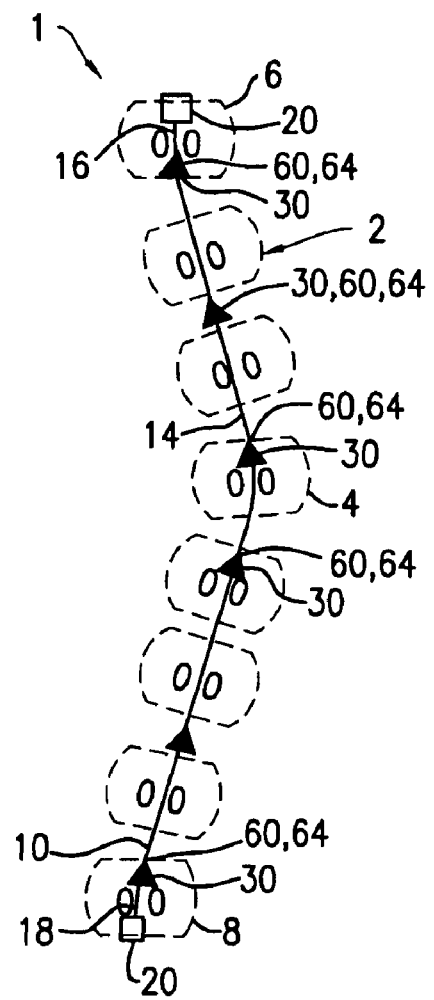
FIGS. 7a and 7b show a seventh embodiment of the correction device, where a blocking element is provided in a single rod system and a dual rod system, respectively.
Figure 7B:
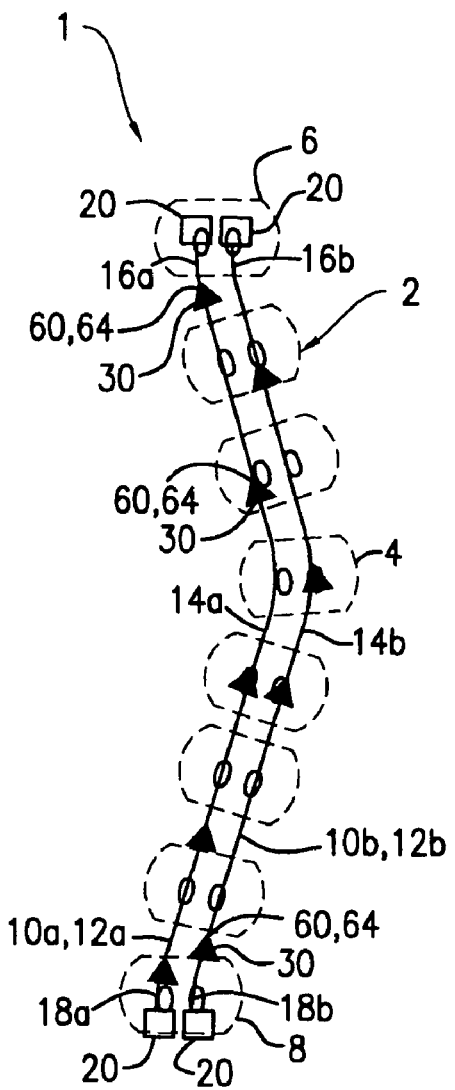

Additionally or alternatively, the restraining element 60 can be in the form of one or more blocking elements 64 for restraining the movement of the support members 10, 10a, and 10b, such as shown in FIGS. 7a and 7b. In an exemplary embodiment, the blocking elements 64 can be placed on the securing elements 20. In another exemplary embodiment, the blocking elements 64 can be placed on the corresponding upper and lower vertebrae 6 and 8 of instrumented spine 2. Exemplary blocking elements 64 can include, but are not limited to, screws, screws with washers, or similar devices.

In one exemplary embodiment, when the superelastic support member 10 restores to its original position after being implanted, the blocking elements 64 can act as a stop mechanism to intercept the movement of the support member 10. The blocking elements 64 can instantaneously stop the movement of the support member 10 without any manual or remote control means. It will be appreciated that other embodiments of the restraining elements 60 are also within the scope of the present invention.

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive.

What is claimed is:

1. A method of providing a constant or substantially constant force for correcting spinal deformities in a human patient, the method comprising:
   providing a correction device comprising an elongated rod, the elongated rod having a pre-contoured shape of a normal degree of kyphosis and lordosis of at least a portion of the patient's spine, the elongated rod comprising a superelastic material having a transition temperature (Af) within the range of human body temperature;
   deforming the elongated rod to conform to a deformed portion of the patient's spine;
   mounting the deformed elongated rod to the patient's spine including the deformed portion, whereby the deformed elongated rod is capable of applying a correction force having a predetermined amount to correct the deformed portion of the patient's spine, the correction force being generated by the superelastic material at the patient's body temperature and in an austenite phase of the superelastic material; and
   maintaining the correction force at the predetermined amount until the deformed elongated rod resumes the pre-contoured shape to fully or substantially fully correct the spinal deformities;
   wherein the correction force is constant or substantially constant and controllable during spinal deformity correction, and wherein the spinal deformity is a deformity of scoliosis, kyphosis, or lordosis; and
   wherein the elongated rod is deformed before or simultaneously when the elongated rod is mounted to the patient's spine including the deformed portion.

2. The method of claim 1, wherein the predetermined amount of the correction force can be adjusted.

3. The method of claim 1, wherein the correction force is activated during the spine correction surgery.

4. The method of claim 1, wherein the correction force is applied to the deformed spine portion from the anterior aspect of the spine.

5. The method of claim 1, wherein the correction force is applied to the deformed spine portion from the posterior aspect of the spine.

6. The method of claim 1 further comprising limiting the correction device from movement.

7. The method of claim 1 further comprising limiting the correction device from a rotation movement.

8. A method of providing a constant or substantially constant force for correcting spinal deformities of a human patient, the method comprising:
   providing a supporting member comprising a superelastic material for generating a correction force having a predetermined amount, the superelastic material having a transition temperature (Af) within the range of human body temperature, the supporting member having a pre-contoured shape of a normal degree of kyphosis and lordosis of at least a portion of the patient's spine;
   applying the correction force to a deformed portion of the patient's spine; and
   maintaining the correction force at the predetermined amount until the spinal deformities are fully or substantially fully corrected;
   wherein the supporting member generates the correction force at the patient's body temperature and in an austenite phase of the superelastic material, and wherein the spinal deformity being corrected is a deformity of scoliosis, kyphosis, or lordosis.

9. The method of claim 8 further comprising deforming at least a portion of the supporting member to conform to the spinal deformities.

10. The method of claim 8, wherein the predetermined amount of the correction force can be adjusted.

11. The method of claim 8, wherein the correction force is activated during the spine correction surgery.

12. The method of claim 8 further comprising limiting the supporting member from movement.

13. The method of claim 8 further comprising limiting the supporting member from a rotation movement.

14. The method of claim 8 further comprising providing an anchor member for mounting the supporting member to the deformed spine portion.

15. The method of claim 14, wherein the anchor member comprises a superelastic material.

16. A method of correcting a spinal deformity of a recipient, the method comprising:
   providing a supporting member comprising a superelastic material;
   deforming the supporting member and mounting the deformed supporting member to a deformed spinal portion of a recipient;
   generating a correction force at the recipient's body temperature and in an austenite phase of the superelastic material, the superelastic material having a transition temperature (Af) within the range of human body temperature; and
   maintaining the correction force until the spinal deformity is fully or substantially fully corrected, wherein the spinal deformity is a deformity of scoliosis, kyphosis, or lordosis;
   wherein the supporting member has a pre-contoured shape of a normal degree of kyphosis and lordosis of the recipient's spine.

17. The method of claim 1, wherein the correction force is not remotely activated.

18. The method of claim 8, wherein the correction force is not remotely activated.

19. The method of claim 16, wherein the correction force is not remotely activated.

20. The method of claim 1, wherein deforming the elongated rod comprising bending the elongated member to conform to the deformed portion of the patient's spine.

21. The method of claim 8, wherein applying the correction force comprising bending the supporting member to conform to the deformed portion of the patient's spine and mounting the bent supporting member to the patient's spine including the deformed portion.

22. The method of claim 16, wherein applying a supporting member comprising bending the supporting member to conform to the deformed spinal portion of the recipient and mounting the bent supporting member to the recipient's spine including the deformed spinal portion.

23. The method of claim 1, wherein the elongated rod is deformed by an orthopedic surgeon during an orthopedic procedure.

24. The method of claim 8, wherein the elongated rod is deformed by an orthopedic surgeon during an orthopedic procedure.

25. The method of claim 16, wherein the elongated rod is deformed by an orthopedic surgeon during an orthopedic procedure.

* * * * *